(12) United States Patent
Kolb et al.

(10) Patent No.: US 6,900,312 B2
(45) Date of Patent: May 31, 2005

(54) THIAZOLE-SUBSTITUTED β-LACTAMS

(75) Inventors: Juergen Kolb, Munich (DE); Alexander Doemling, Munich (DE)

(73) Assignee: Priaton GmbH, Munich (DE)

( * ) Notice: Subject to any disclaimer, the term of this patent is extended or adjusted under 35 U.S.C. 154(b) by 0 days.

(21) Appl. No.: 10/196,052

(22) Filed: Jul. 16, 2002

(65) Prior Publication Data

US 2003/0119671 A1 Jun. 26, 2003

(30) Foreign Application Priority Data

Jul. 16, 2001 (DE) .......................................... 101 34 478

(51) Int. Cl.⁷ ........................ C07D 417/06; A61P 31/04
(52) U.S. Cl. ................... 540/200; 540/354; 540/360; 540/361; 540/362; 540/363; 562/26
(58) Field of Search ................................ 540/200, 354, 540/360, 361, 362, 363; 514/210.02

(56) References Cited

U.S. PATENT DOCUMENTS 6,242,439 B1 * 6/2001 Yoakim et al. ........ 514/210.02

FOREIGN PATENT DOCUMENTS

WO      WO 97/21676     *  6/1997

* cited by examiner

*Primary Examiner*—Mark L. Berch
(74) *Attorney, Agent, or Firm*—Frommer Lawrence & Haug LLP; Ronald R. Santucci

(57) ABSTRACT

The present discovery consists in new thiazole-substituted β-lactams of general formula (I), as well as the method for their preparation.

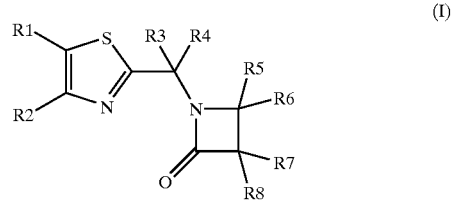

(I)

R1, R2, R3, R4, R5, R6, R7, and R8 are, independently from each other, a hydrogen atom, a halogen, a hydroxy, amino, nitro, or thiol group, an optionally substituted alkyl, heteroalkyl, aryl, aralkyl, cycloalkyl, cycloaralkyl, heterocycloalkyl, heteroaralkyl, or heteroaryl rest.

9 Claims, No Drawings

THIAZOLE-SUBSTITUTED β-LACTAMS

This application claims priority benefits of German patent application number DE 101 34 478.3 filed Jul. 16, 2001.

The present invention relates to new thiazole-substituted β-lactams, and a method for their preparation. Such compounds are above all of tremendous interest for pharmaceutical chemistry, e.g. as antibiotics.

The β-Lactams still represent the most important class of antibiotics. Most of them are bicyclic molecules, to which penicillins and cephalosporins belong among others. Some monocyclic β-lactams also have pharmacological uses, as for example monobactams.

The object of the present invention was to provide new bicyclic β-lactams, and a procedure for their synthesis.

It was found that through the use of a β-amino-thiocarboxylic acid the synthesis of a β-lactam through the Ugi-4-centered-3-component reaction (I. Ugi, J. prakt. Chem. 1997, 339, 499–516; A. Dömling, I. Ugi, Angew. Chem. Int. Ed. 2000, 39, 3168–3210) can be combined with a thiazole synthesis (S. Heck, A. Dömling, Synlett 2000, 424–426). By such a reaction, we obtained a bi-heterocyclic compound with the general formula (I)

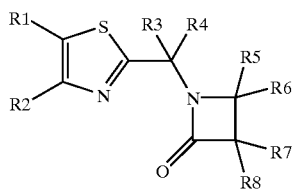

wherein

R1, R2, R3, R4, R5, R6, R7, and R8 are independently from each other, a hydrogen atom, a halogen atom, a hydroxy-, amino-, nitro-, or thiol-group, an optionally substituted alkyl-, heteroalkyl-, aryl-, aralkyl-, cycloalkyl-, cycloaralkyl-,heterocycloalkyl-, hetero-aralkyl, or heteroarylgroup.

The term alkyl refers to a saturated or an unsaturated, an unbranched or a branched alkyl-group, that contains of 1 to 20 carbon atoms, preferably 1 to 12 carbon atoms, especially preferably 1 to 7 carbon atoms, for example the methyl, ethyl, isopropyl, isobutyl, tert-butyl, n-hexyl, 2,2-dimethylbutyl, n-octyl, allyl, isoprenyl, or the hex-2-enyl group.

The term heteroalkyl refers to an alkyl group, in which one or more carbon atoms are replaced by an oxygen, nitrogen, phosphorus or sulfur, for example the methoxy or ethoxy, or a methoxymethyl, nitrile, methylcarboxyalkylester, carboxyalkylester, or 2,3-dioxyethyl group.

The term cyclo refers to a saturated or a partly unsaturated, cyclic or a branched cylic group, that contains of one or more rings, which form a structure, that contains 3 to 14 carbon atoms, especially 5 or 6 up to 10 carbons. These are for example the cyclopropyl, cyclohexyl, tetralin, or cyclohex-2-enyl groups.

The term heterocylco refers to a carbocyclic group, in which one or more carbon atoms are replaced by an oxygen, a nitrogen, a phosphorus, or a sulfur atom. Furthermore, a heterocycloalkyl group can be substituted by an alkyl, heteroalkyl or an aryl group. It can represent, for example, a piperidine, morpholine, n-methyl-piperazine or n-phenylpiperazine group.

The terms aryl and ar refer to an aromatic cyclic or branched cyclic group, which has one or more rings containing a carbon backbone that contains of 5 to 14, especially 5 or 6 to 10 carbon atoms. In addition, an aryl group can be substituted by an alkyl or an heteroalkyl group and can, for example, be a phenyl, naphthyl, 2-, 3- or 4-methoxyphenyl, 2-, 3-, or 4-ethoxyphenyl, 4-carboxyphenylalkyl, or 4-hydroxyphenyl group.

The term heteroaryl refers to an aryl group, in which one or more carbon atoms are replaced by an oxygen, a nitrogen, a phophorus or a sulfur, for example the 4-pyridyl, 2-imidazolyl, 3-pyrazolyl and isochinolinyl group.

The terms aralkyl and heteroaralkyl respectively, refer to groups, that suitably encompass the above definitions of aryl and heteroaryl, respectively, as well as alkyl and/or heteroalkyl and/or carbocyclic groups and/or heterocycloalkyl ring-systems, for example the tetrahydro-isochinolinyl, benzyl, 2- or 3-ethylindolyl or 4-methylpyridino group.

The terms alkyl, heteroalkyl, cyclo, heterocycloalkyl, aryl, heteroaromatic and aralkyl refer also to groups, in which one or more hydrogens of such groups are substituted by fluorine, chlorine, bromine or iodine. Furthermore, these terms will refer to groups that are substituted with unsubstituted alkyl, heteroalkyl, aralkyl or aralkyloxy groups.

The compounds with general formula (I) are preferred, wherein R1, R2, R3, R4, R5, R6, R7 and R8, independently from each other, represent a hydrogen, an optionally substituted alkyl, heteroalkyl, aryl, aralkyl, cycloalkyl, cycloaralkyl, heterocyclo-alkyl, heteroaralkyl or heteroaryl rest.

Furthermore, the compounds with general formula (I), wherein R1 is a hydrogen, are especially preferred.

The compounds with general formula (I), wherein R3 is not a hydrogen atom, are also especially preferred. Preferably R3 is a halogen atom, a hydroxy-, amino-, nitro-, or thiol-group, an optionally substituted alkyl-, heteroalkyl-, aryl-, aralkyl-, cycloalkyl-, cycloaralkyl-, heterocycloalkyl-, hetero-aralkyl, or heteroarylgroup.

The compounds with general formula (I), wherein R7 and R8 are hydrogen atoms are also preferred.

The compounds with general formula (I), wherein R2 is a group with the formula COOR9, wherein R9 is a hydrogen atom, an optionally substituted alkyl, heteroalkyl, aryl, aralkyl, cycloalkyl, cycloaralkyl, heterocycloalkyl, heteroaralkyl, or heteroaryl rest, are also preferred.

The compounds with general formula (I), wherein R5 and R6 are independently from each other, a hydrogen atom or a group whose formula is CR14R15, wherein R14 and R15 independently represent a hydrogen atom, an optionally substituted alkyl, heteroalkyl, aryl, aralkyl, cycloalkyl, cycloaralkyl, heterocycloalkyl, heteroaralkyl, or heteroaryl rest and n=0, 1, 2, or 3.

The compounds according to the present invention can be synthesized through the reaction of the compounds with the general formulas II, III, IV.

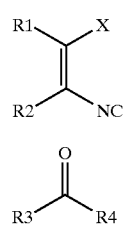

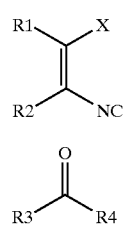

-continued

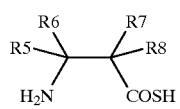

(IV)

wherein the rests are as described above, and X is a leaving group such as F, Cl, Br, I, NR10R11, OR12 or SOnR13, where R10, R11, R12, and R13 are, independently from each other a hydrogen atom, an optionally substituted alkyl, heteroalkyl, aryl, aralkyl, cycloalkyl, cycloaralkyl, heterocycloalkyl, heteroaralkyl, or heteroaryl rest and n=0, 1, 2, or 3.

The groups X=F, Cl, Br, I, or NR10R11 are preferred.

X=N(Me)$_2$ are especially preferred.

The alcohols such as methanol, ethanol or benzylalcohol are preferred as solvents. Preferably, the reaction is carried out under exclusion of water.

The invention also includes pharmaceutical compositions which contain at least one compound of formula I.

EXAMPLES

General Procedure

Under inert gas atmosphere and stringently water-free conditions, 5 mmol of the β-amino thio-acid (IV) (the synthesis is carried out in a similar way as for the corresponding α-amino thio-acid: T. Wieland, K. E. Euler, Chem. Ber. 1958, 91, 2305–2308) are added to 10 ml of methanol with an equimolar amount of MgSO$_4$. Under cooling at a temperature of −15° C., 5 mmol of the aldehyde, especially ketones (III), respectively, are added dropwise in 5 ml of methanol. The reaction mixture is refluxed overnight. Then 5 mmol of the isocyanide (II) are added at a low temperature (U. Schöllkopf et al., Liebigs Ann. Chem. 1979, 1444–1446) in 10 ml of methanol. The reaction mixture will be left to react for one day at RT (if needed, the mixture can be heated at a temperature of 40–50° C.). The progress of the reaction can be controlled by TLC.

When the isonitrile has reacted, methanol is removed under vacuum. The residue is diluted in 40 ml of dichloromethane and subsequently washed with 1% phosphorus acid, a saturated solution of sodium hydrogen carbonate and water. The organic phase can be dried with Na$_2$SO$_4$ and the solvent can be removed it under vacuum. The purification is carried out through column chromatography.

Synthesized examples: R1, R6, R7, R8=H

| R2 | R3 | R4 | R5 | Yield | Molecular Formula (M) | MS (M + H) |
|---|---|---|---|---|---|---|
| COOMe | H | (CH$_3$)$_2$CH | Me | 69% | C13H18N2O3S (282.36) | 283 |
| COOMe | H | (CH$_3$)$_2$CH | H | 59% | C12H16N2O3S (268.34) | 269 |
| COOMe | Me | Me | H | 50% | C11H14N2O3S (254.31) | 255 |
| COOtBu | H | (CH$_3$)$_2$CH | Me | 44% | C16H24N2O3S (324.57) | 325 |
| 4-C$_5$H$_4$N | H | (CH$_3$)$_2$CH | Me | 66% | C16H19N3OS (301.41) | 302 |

What is claimed is:

1. Compounds of general formula (I):

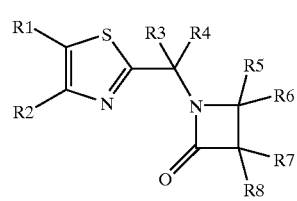

(I)

wherein R1, R2, R3, R4, R5, R6, R7 and R8 are, independently from each other, a hydrogen, an optionally substituted alkyl, heteroalkyl, aryl, aralkyl, cycloalkyl, heterocycloalkyl, heteroaralkyl, or heteroaryl group.

2. Compounds of claim 1, wherein R3 is a halogen, a hydroxy, amino, nitro or thio group, an optionally substituted alkyl, heteroalkyl, aryl, aralkyl, cycloalkyl, heterocycloalkyl, heteroaralkyl, or heteroaryl group.

3. Compounds of claim 1, wherein R2 is a group with formula COOR9, wherein R9 is a hydrogen, an optionally substituted alkyl, heteroalkyl, aryl, aralkyl, cycloalkyl, heterocycloalkyl, heteroaralkyl, or heteroaryl group.

4. Compounds of claim 1, wherein R5 and R6 are, independently from each other, a hydrogen or a group with formula CR14R15, wherein R14 and R15 are, independently from each other, a hydrogen, an optionally substituted alkyl, heteroalkyl, aryl, aralkyl, cycloalkyl, heterocycloalkyl, heteroaralkyl, or heteroaryl group.

5. A method for the production of compounds of claim 1, wherein the compounds with formula II, III and IV react with each other,

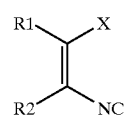

(II)

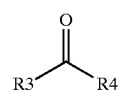

(III)

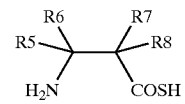

(IV)

wherein the groups are defined as in claim 2, and X is F, Cl, Br, I, NR10R11, OR 12 or SOnR13, wherein R10, R11, R12 and R13 are, independently from each other, a hydrogen, an optionally substituted alkyl, heleroalkyl, aryl, aralkyl, cycloalkyl, heterocycloalkyl, heteroaralkyl, or heteroaryl group and n=0, 1, 2, or 3.

6. The method of claim 5, where X=F, Cl, Br, I or NR10R11.

7. The method of claim 5, where X=N(Me)2.

8. The method of claim 5, wherein an alcohol is used as solvent.

9. The method of claim 5, wherein the reaction is earned out under humidity-free conditions.

* * * * *